United States Patent
Choi et al.

(10) Patent No.: US 10,352,819 B2
(45) Date of Patent: Jul. 16, 2019

(54) METHOD OF MEASURING TRANSMISSION CHARACTERISTICS OF OPTICAL TRANSFER MEDIUM AND IMAGE ACQUISITION DEVICE USING THE SAME

(71) Applicant: KOREA UNIVERSITY RESEARCH AND BUSINESS FOUNDATION, Seoul (KR)

(72) Inventors: Won-Shik Choi, Seoul (KR); Dong-Gyu Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 29 days.

(21) Appl. No.: 15/102,673

(22) PCT Filed: Feb. 26, 2014

(86) PCT No.: PCT/KR2014/001561
§ 371 (c)(1),
(2) Date: Jun. 8, 2016

(87) PCT Pub. No.: WO2015/088102
PCT Pub. Date: Jun. 18, 2015

(65) Prior Publication Data
US 2016/0299033 A1 Oct. 13, 2016

(30) Foreign Application Priority Data
Dec. 13, 2013 (KR) .................. 10-2013-0155281

(51) Int. Cl.
*G01M 11/00* (2006.01)
*G01N 21/59* (2006.01)

(52) U.S. Cl.
CPC ............ *G01M 11/33* (2013.01); *G01N 21/59* (2013.01)

(58) Field of Classification Search
CPC .................................................... G01M 11/33
(Continued)

(56) References Cited

U.S. PATENT DOCUMENTS

2002/0057431 A1    5/2002  Fateley et al.
2003/0076571 A1*   4/2003  MacAulay .......... G02B 21/0028
                                                    359/237
(Continued)

FOREIGN PATENT DOCUMENTS

JP       2008-249577 A    10/2008
KR    10-2012-0053710 A    5/2012
KR       10-1287738 B1     7/2013

OTHER PUBLICATIONS

Donggyu Kim, Jungho Moon, Moonseok Kim, Taeseok Daniel Yang, Jaisoon Kim, Euiheon Chung and Wonshik Choi; Pixelation-free and Real-time Endoscopic Imaging through a Fiber Bundle, Aug. 30, 2013, Cornell University Library, vol. 1., pp. 1-17 (Year: 2013).*

(Continued)

*Primary Examiner* — Tarifur R Chowdhury
*Assistant Examiner* — Omar H Nixon
(74) *Attorney, Agent, or Firm* — NSIP Law

(57) ABSTRACT

A image acquisition device comprises a light source unit, a digital micro mirror, an optical transfer medium, an imaging unit, and a beam splitter, wherein a single focusing pattern light is formed to be focused on a single specific point when the focusing pattern light penetrates the optical transfer medium, and specific points focused by each of the plurality of focusing pattern lights scan the object to be measured such that the object to be measured is imaged. Therefore, when an image is obtained through an optical transfer medium such as an optical fiber, pixelation and aberration can be avoided regardless of the type of optical transfer (Continued)

medium and an image having high resolution can be obtained fast without a separate scanner.

12 Claims, 10 Drawing Sheets

(58) Field of Classification Search
  USPC ........................................................ 356/73.1
  See application file for complete search history.

(56) References Cited

U.S. PATENT DOCUMENTS

| | | | |
|---|---|---|---|
| 2005/0213092 A1* | 9/2005 | MacKinnon | G01J 1/32 356/336 |
| 2007/0173718 A1* | 7/2007 | Richards-Kortum | A61B 1/00096 600/431 |
| 2007/0263226 A1 | 11/2007 | Kurtz et al. | |
| 2009/0046298 A1* | 2/2009 | Betzig | G01N 21/6445 356/521 |
| 2011/0009701 A1 | 1/2011 | Feldman et al. | |
| 2014/0320835 A1* | 10/2014 | Fujiwara | G02B 26/06 355/67 |

OTHER PUBLICATIONS

International Search Report dated Aug. 14, 2014 in corresponding International Application No. PCT/KR2014/001561 (7 pages in Korean with English translation).

* cited by examiner (a)                    (b)

(a)

(b)

METHOD OF MEASURING TRANSMISSION CHARACTERISTICS OF OPTICAL TRANSFER MEDIUM AND IMAGE ACQUISITION DEVICE USING THE SAME

CROSS REFERENCE TO RELATED APPLICATION(S)

This application is a National Phase entry of PCT Application No. PCT/KR2014/001561, filed on Feb. 26, 2014, which claims priority under 35 U.S. C. § 119(e), 120 and 365(c) to Korean Patent Application No. 10-2013-0155281, filed on Dec. 13, 2013, in the Korean Intellectual Property Office, the entire disclosures of each of which are incorporated herein by reference for all purposes.

TECHNICAL FIELD

The invention relates to a method of measuring transmission characteristics of an optical transfer medium and an image acquisition device using the same and in particular, to a method of measuring transmission characteristics of an optical transfer medium and an image acquisition device using the same to avoid pixelation and increase resolution during the image acquisition through the optical transfer medium such as an optical fiber.

BACKGROUND ART

Image acquisition method using optical transfer medium such as optical fibers are widely being used for medical instruments including medical endoscope, industrial devices for inspecting sewer pipes, an inner part of a collapsed building, an inner structure of a building, etc. For example, endoscope devices using optical fibers are disclosed in Korean laid-open patent publication Nos. 10-2005-0111011, Korean patent publication 10-0945280, etc.

In general, image acquisition techniques using optical fibers can be divided into a scanner-free method and a scanning method. Here, in case of the scanner-free method, since a single optical fiber cannot transfer image for the wide area, the scanner-free method uses an optical fiber bundle instead of a single optical fiber.

In case of scanner-free method, a number of bundled optical fibers are arranged at the input and the output in the same order such that the intensity of light which is transferred through one optical fiber at the input becomes one point at the output. A lens for imaging is attached to one end of the optical fiber bundle so that an image of object is formed at the end of the bundle and then each optical fiber constituting the bundle transfers image pixels to the outside. The advantage of the scanner-free method is that an image of object can be obtained for wide area in real time without need to analyze an image.

However, in the scanner-free method, since a number of optical fibers are needed to obtain high resolution, a diameter of the optical fiber bundle must be enlarged. Further, the optical fiber bundle having many of optical fibers is less flexible, and the number of bad pixels increases when the optical fiber is cut as time goes by. Further, if a thick bundle is inserted into a patient's body, the bundle is contact with a living body's tissue, thereby causing a severe friction. Therefore, the friction generates inconveniences such as pain and even a destruction of inner tissues.

Also, there is another problem that a pixelation of image occurs and thus, the quality of image is decreased. Referring to FIG. 1, FIG. 1(a) shows an image obtained with the optical fiber bundle and each of optical fiber constituting an optical fiber bundle forms one pixel in the image.

FIG. 1(b) shows an example of a target image which is a cell of a human body. As shown in FIGS. 1(a) and (b), if the size of a sample, e.g., cell, in the target image is less than the diameter of the optical fiber constituting an optical fiber bundle, an image is pixelated and the sample is hardly discerned as shown in FIG. 1(c). The resolution of the image is determined by the number of optical fibers constituting the optical fiber bundle and thus, the resolution of the image is low as can be seen in FIG. 1(c).

As an alternative to the scanner-free method, a scanning method is provided. In the scanning method, a condensing lens and a scanner are attached to the end of a single optical fiber and an object to be measured is scanned in a scanning method. In the scanner-free method, light is focused on one point at a time and a reflected light is obtained through an optical fiber. Therefore, to obtain an image over a wide area, a scanner must be installed to scan focused light.

As such, in the scanner-free method, it is advantageous that the diameter can be very small since a single optical fiber is used. However, since a lens and a scanner must be installed at the end of the fiber, the reduction of diameter is not substantial. Further, a further element such as a scanner must be installed and the image acquisition rate is low due to the scanning speed of the scanner. Moreover, the image quality is decreased by malfunction of the scanner.

DISCLOSURE OF THE INVENTION

Technical Problem

The invention is intended to solve the above problems and provides a method of measuring transmission characteristics of an optical transfer medium and an image acquisition device using the same to avoid pixelation and aberration regardless of the type of optical transfer medium during an image acquisition through an optical transfer medium such as an optical fiber and to obtain an image having high resolution fast without a separate scanner.

Technical Solution

The object of the invention may be accomplished by a method for measuring transmission characteristics of optical transfer medium comprising the following steps: (a) irradiating light from a light source unit; (b) reflecting light irradiated from the light source unit by a digital micro mirror and making the light penetrate the optical transfer medium, wherein a plurality of random pattern lights having different wave surfaces are generated subsequently according to on/off pattern of a plurality of unit mirrors constituting the digital micro mirror and then penetrate the optical transfer medium; (c) imaging transmission light which penetrated the optical transfer medium at the step (b) subsequently; (d) measuring a transmission matrix for the transmission characteristics of the optical transfer medium based on the plurality of random pattern lights and the transmission light imaged at the step (c); and (e) obtaining a plurality of focusing pattern lights for on/off pattern of the digital micro mirror based on the transmission matrix; wherein a single focusing pattern light is configured to be focused on a single specific point when the focusing pattern light penetrates the optical transfer medium, and specific points focused by each of the plurality of focusing pattern lights are configured to scan the object to be measured such that the object to be measured is imaged.

Herein, the optical transfer medium may comprise, inside the medium, a plurality of light paths which are independent each other and during the step (b), a mode-mixing may be made on light which penetrates the plurality of light paths and then the light may be emitted from the optical transfer medium.

Also, the optical transfer medium may comprise an optical fiber bundle having a plurality of optical fibers each of which forms each light path.

Further, the optical transfer medium may comprise at least one of a graded index lens having cylindrical shape and a medium applied to image acquisition which allows light to penetrate the medium and which generates light distortion inside the medium.

Further, the transmission matrix may comprise phase information of light reflected by each unit mirror at the specific point of light which penetrated the optical transfer medium; and during the step (e), the focusing pattern light for one specific point may be obtained such that the unit mirrors which reflected light which forms constructive interference at the corresponding specific point based on the phase information are turned on.

Further, the digital micro mirror may be configured such that each of the unit mirrors is turned on/off independently or adjacent unit mirrors are turned on/off by N×M mirrors to form the random pattern light.

Moreover, at the step (e), the plurality of focusing pattern lights may be obtained by each distance from the object to be measured.

The object of the invention may be also accomplished by an image acquisition device comprising: a light source unit which irradiates light; a digital micro mirror which consists of a plurality of unit mirrors and which reflects light irradiated from the light source unit such that a plurality of predetermined focusing pattern lights having different wave surfaces are generated subsequently according to on/off pattern of the plurality of unit mirrors; an optical transfer medium which allows the focusing pattern lights formed by the digital micro mirror to penetrate the optical transfer medium and then to move toward an object to be measured; an imaging unit which images object light which was reflected by the object to be measured and penetrated the optical transfer medium; and a beam splitter arranged on a light path between the digital micro mirror and the optical transfer medium to direct the focusing pattern light from the digital micro mirror toward the optical transfer medium and to direct the object light which penetrated the optical transfer medium toward the imaging unit, wherein a single focusing pattern light is formed to be focused on a single specific point when the focusing pattern light penetrates the optical transfer medium, and specific points focused by each of the plurality of focusing pattern lights scan the object to be measured such that the object to be measured is imaged.

Here, each of the plurality of focusing pattern lights may be configured to be focused on each specific point based on transmission matrix which is premeasured for the optical transfer medium; and wherein the transmission matrix may be measured by the following steps: (a) irradiating light from a light source unit; (b) reflecting light irradiated from the light source unit by a digital micro mirror and making the light penetrate the optical transfer medium, wherein a plurality of random pattern lights are generated subsequently according to on/off pattern of a plurality of unit mirrors and then penetrate the optical transfer medium; (c) imaging transmission light which penetrated the optical transfer medium at the step (b) subsequently; and (d) measuring the transmission matrix for the optical transfer medium based on the plurality of random pattern lights and the transmission light imaged at the step (c).

Further, the transmission matrix may comprise phase information of light reflected by each unit mirror at the specific point of light which penetrated the optical transfer medium; and the focusing pattern light for one specific point is configured such that the unit mirrors which reflected light which forms constructive interference at the corresponding specific point based on the phase information are turned on.

Here, the digital micro mirror may be configured such that each of the unit mirrors is turned on/off independently or adjacent unit mirrors are turned on/off by N×M mirrors to form the random pattern light.

Further, the optical transfer medium may comprise, inside the medium, a plurality of light paths which are independent each other and the image acquisition device further comprises an object lens arranged the beam splitter and the optical transfer medium so that a mode-mixing is made on light which penetrates the plurality of light paths and then the light is emitted from the optical transfer medium.

Here, the optical transfer medium may comprise an optical fiber bundle having a plurality of optical fibers each of which forms the plurality of light paths.

Further, the optical transfer medium may comprise at least one of a graded index lens having cylindrical shape and a medium applied to image acquisition which allows light to penetrate the medium and which generates light distortion inside the medium.

Further, the plurality of focusing pattern lights may be obtained and recorded by each distance from the object to be measured.

Advantageous Effect

According to the above features, when an image is obtained through an optical transfer medium such as an optical fiber, a method of measuring transmission characteristics of an optical transfer medium and an image acquisition device using the same is provided which can avoid pixelation and aberration regardless of the type of optical transfer medium and obtain an image having high resolution fast without a separate scanner.

BEST MODE FOR CARRYING OUT THE INVENTION

A method for measuring transmission characteristics of optical transfer medium according to the invention is characterized in that it comprises the following steps: (a) irradiating light from a light source unit; (b) reflecting light irradiated from the light source unit by a digital micro mirror and making the light penetrate the optical transfer medium, wherein a plurality of random pattern lights having different wave surfaces are generated subsequently according to on/off pattern of a plurality of unit mirrors constituting the digital micro mirror and then penetrate the optical transfer medium; (c) imaging transmission light which penetrated the optical transfer medium at the step (b) subsequently; (d) measuring a transmission matrix for the transmission characteristics of the optical transfer medium based on the plurality of random pattern lights and the transmission light imaged at the step (c); and (e) obtaining a plurality of focusing pattern lights for on/off pattern of the digital micro mirror based on the transmission matrix; wherein a single focusing pattern light is configured to be focused on a single specific point when the focusing pattern light penetrates the optical transfer medium, and specific points focused by each of the plurality of focusing pattern lights are configured to scan the object to be measured such that the object to be measured is imaged.

MODE FOR CARRYING OUT THE INVENTION

Hereinafter, embodiments according to the invention will be explained in detail referring to the attached drawings.

Figure 1:
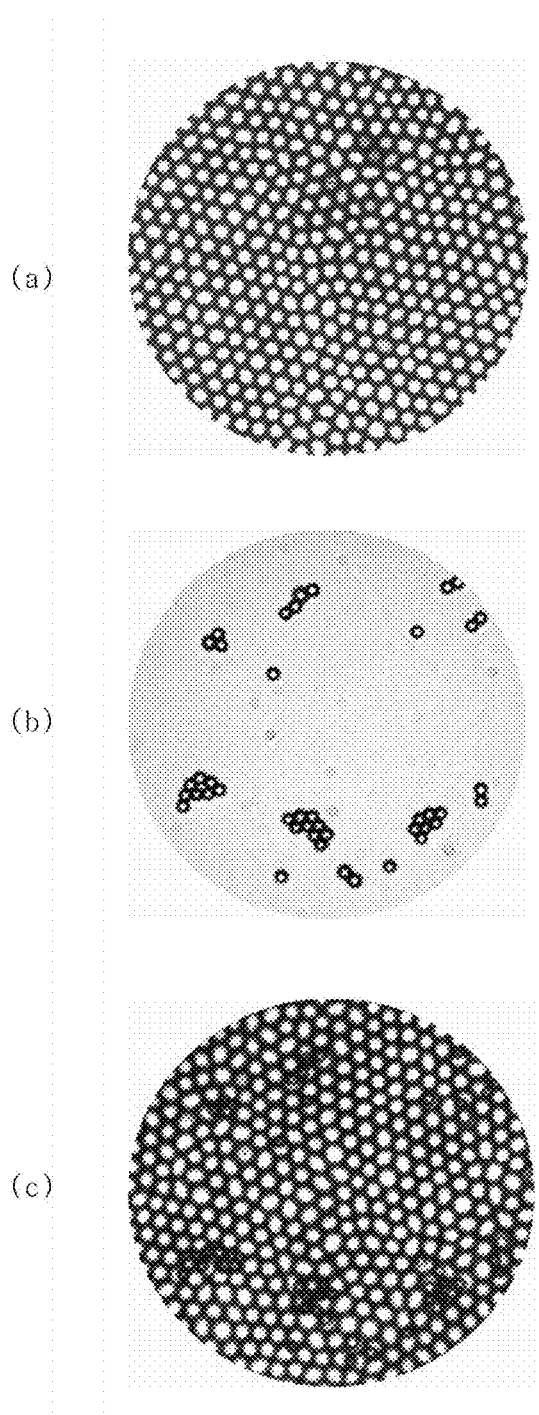
FIG. 1 describes a pixelation effect which occurs by the image acquisition method of prior arts.
Figure 2:
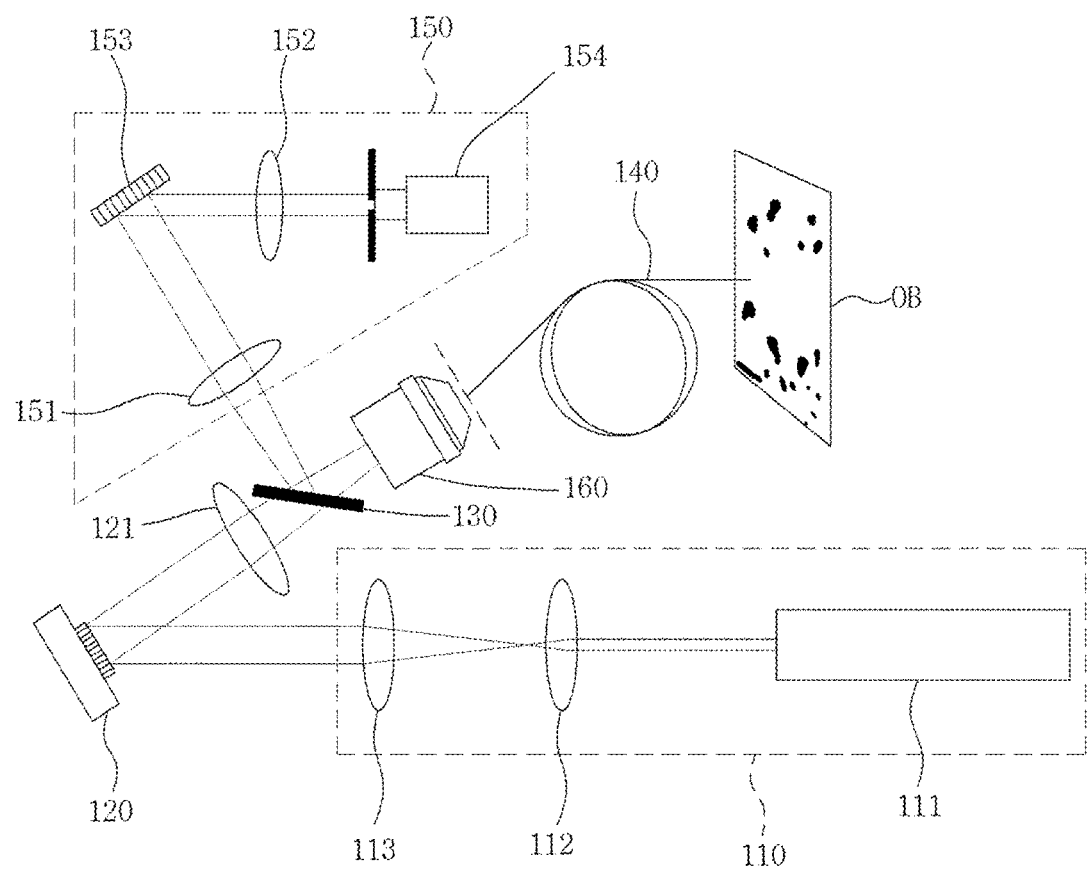
FIG. 2 represents an image acquisition device according to the present invention.

FIG. 2 represents an image acquisition device according to the present invention. The image acquisition device in FIG. 2 shows an example of a medical endoscope. Referring to FIG. 2, the image acquisition device comprises a light source unit 110, a digital micro mirror 120, an optical transfer medium 140, an imaging unit 150 and a beam splitter 130.

The light source unit 110 illuminates a light to obtain an image. In the embodiment, the light source unit 110 comprises a light source 111, a condensing lens 112 for collecting light from the light source 111 and a projection lens 113 for converting the light collected by the condensing lens 112 into parallel light. In the embodiment, a light source 111 is configured as a He—Ne laser light source 111, but the invention is not limited to this embodiment.

Light irradiated from the light source unit 110 is reflected by a digital micro mirror 120 toward the beam splitter 130. Here, a lens 121 may be arranged between the digital micro mirror 120 and the beam splitter 130.

The digital micro mirror 120 is configured as a plurality of unit mirrors. Light irradiated from the light source 111 and reflected by the mirror creates a pattern light whose wave surface is adjusted according to on/off patterns of the plurality of unit mirrors. Hereinafter, the pattern light created by the digital micro mirror 120 during the image acquisition process is referred to as 'focusing pattern light'.

In the embodiment, the on/off pattern of a plurality of unit mirrors varies according to the predetermined pattern such that the digital micro mirror 120 creates a plurality of focusing pattern lights sequentially. Here, a focusing pattern light penetrates an optical transfer medium 140 and then is focused on a specific point. A plurality of specific points focused by each of a plurality of focusing pattern lights created by the digital micro mirror 120 will scan an object to be measured (OB), thereby an image of the object can be obtained. Detailed explanation will be described hereinafter.

The beam splitter 130 is disposed on a light path between the digital micro mirror 120 and the optical transfer medium 140. Here, the beam splitter 130 makes the focusing pattern light from the digital micro mirror 120 propagate toward the optical transfer medium 140. As described above, the focusing pattern light which penetrated the optical transfer medium 140 is focused on a specific point of the object to be measured (OB) and is reflected by the object (OB), and then light (hereinafter referred to as 'object light') reflected from the object (OB) penetrates the optical transfer medium 140 and transfers toward the beam splitter 130.

The object light incident on the beam splitter 130 is reflected by the beam splitter 130 toward the imaging unit 150. In this example, it is described that the focusing pattern light from the digital micro mirror 120 penetrates the beam splitter 130 toward the optical transfer medium 140 and the object light from the optical transfer medium 140 is reflected by the beam splitter 130 toward the imaging unit 150. Alternatively, a light path of the light source unit 110 and the digital micro mirror 120 and a light path of the imaging unit 150 can be changed.

The imaging unit 150 performs imaging for the object light which is reflected by the object to be measured (OB) and which is then incident on the imaging unit sequentially, based on the plurality of focusing pattern lights. In the example, the imaging unit 150 comprises at least one lens 151, 152 disposed on a light path and an imaging device 154 for taking an image. The imaging unit 150 further comprises a diffraction grating 153, but it is not limited to this example. In the embodiment, PMT (Photo Multiplier Tube) may be used for the imaging device 154 constituting the imaging unit 150.

Here, since the focusing pattern light according to the invention penetrates the optical transfer medium 140 and then is focused on a specific point and specific points corresponding to the plurality of focusing pattern lights perform scanning of the object to be measured (OB), the imaging unit 150 creates one image by an object light corresponding to one scanning.

That is, the image acquisition device according to the invention can make an image acquisition of scanning type by means of a plurality of focusing pattern lights which use on/off patterns pre-stored in the digital micro mirror 120, without a separate scanner.

Figure 3:
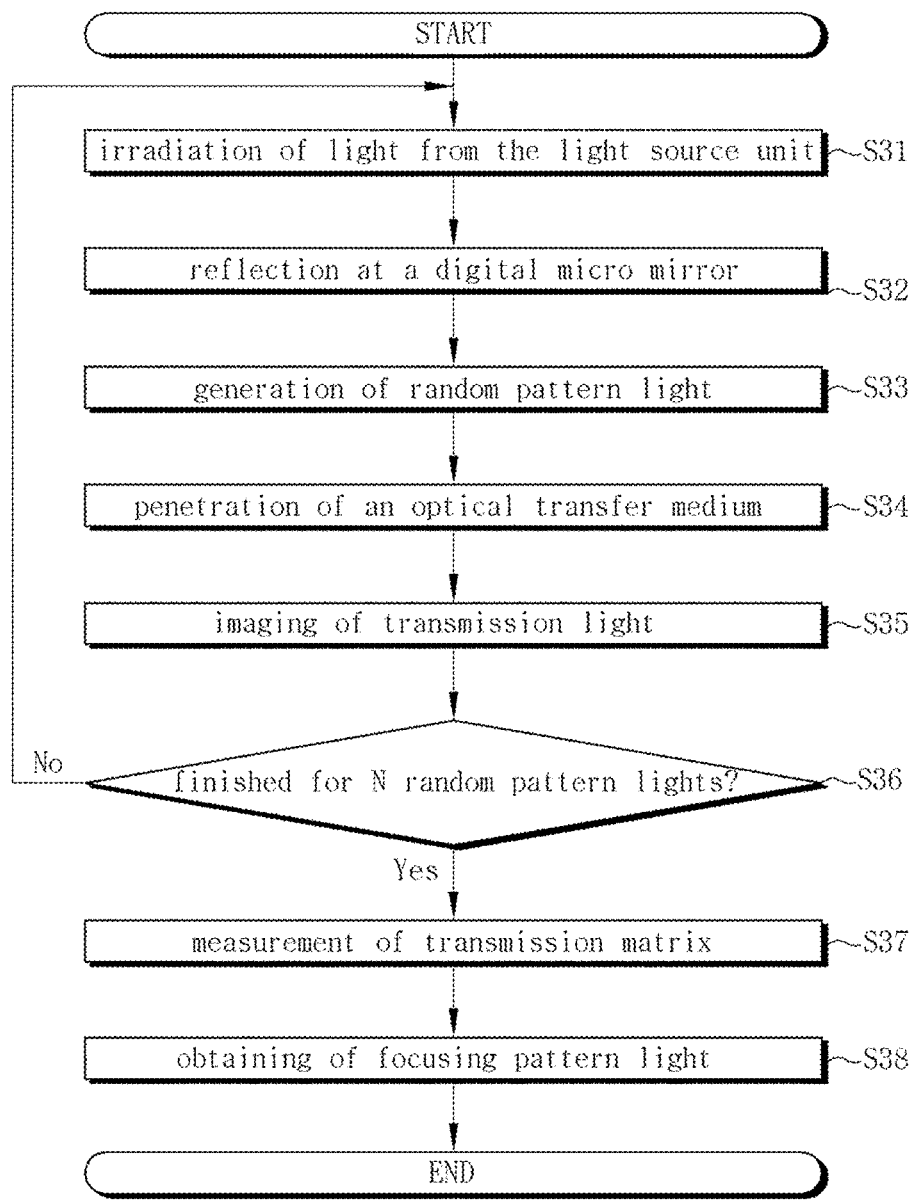
FIG. 3 represents a method of measuring transmission matrix applied to an image acquisition device according to the present invention and producing a plurality of focusing pattern light for optical transfer medium.

Hereinafter, referring to FIG. 3, a method of obtaining a plurality of focusing pattern lights for the optical transfer medium 140 by measuring a transmission matrix applied to the image acquisition device according to the invention will be described in detail.

Here, the transmission matrix reflects transmission characteristics of the optical transfer medium 140.

First, if light is irradiated from the light source unit 110, the light from the light source 111 is reflected by the digital micro mirror 120. At this time, when the light is reflected by the digital micro mirror 120, a plurality of unit mirrors constituting the digital micro mirror 120 is randomly turned on/off such that random pattern light whose wave surface is adjusted is created. (S32)

As such, the random pattern light created by the reflection on the digital micro mirror 120 penetrates the optical transfer medium 140 (S34) and the light which penetrated the optical transfer medium 140 is imaged by the imaging unit 150 (S35).

By making the digital micro mirror 120 turn on/off the unit mirror randomly, the above method is carried out for N random pattern lights having different wave surfaces such that N transmission lights are imaged. Here, the number N of random pattern lights is determined for accurate and precise measurement of the transmission matrix. Considering the response rate of the digital micro mirror 120 having a frame rate of 23 kHz, the measurement time is not long even when several ten thousand of random pattern lights are being imaged.

If the imaging is finished for N random pattern lights S36, a transmission matrix for the optical transfer medium 140 is measured (S37) based on a plurality of random pattern lights created by the digital micro mirror and a plurality of transmission lights imaged during the step S35.

Figure 4:
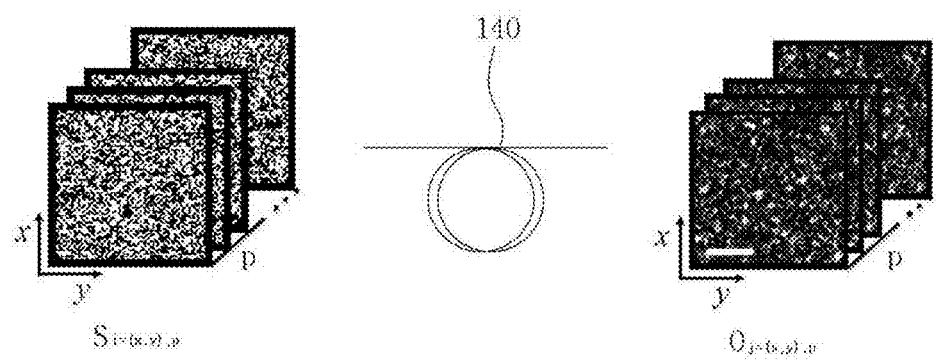
FIGS. 4 to 6 represent schematically a relationship between a plurality of random pattern lights and a plurality of imaged transmission light according to the present invention.

FIG. 4 represents schematically a relationship between a plurality of random pattern lights and a plurality of imaged transmission light and the transmission matrix can be obtained by a matrix formula such as the following formula 1.

$$t_{ij} = \sum_p O_{ip} S_{jp}^{-1} \quad \text{[Formula 1]}$$

Here, the random pattern light and the imaged transmission light have information of phase and size for x, y coordinates, respectively. In the formula 1, $t_{ij}$ is a transmission matrix, $O_{ip}$ is an imaged transmission light, and $S_{jp}$ is a random pattern light.

By the above method, a plurality of focusing pattern lights for the optical transfer medium 140 are obtained by using the measured transmission matrix (S38), which will be described in more detail referring to FIGS. 5 and 6. In an example, for ease of reference, the unit mirrors of the digital micro mirror 120 in FIGS. 5 and 6 consist of 4×4 mirrors, i.e., 16 mirrors.

As described above, in case that the transmission matrix is obtained through the formula 1 by using the plurality of random pattern lights and the imaged transmission lights, the transmission matrix comprises phase information of light reflected by each unit mirror at the specific point of light which penetrated the optical transfer medium 140.

Figure 5:
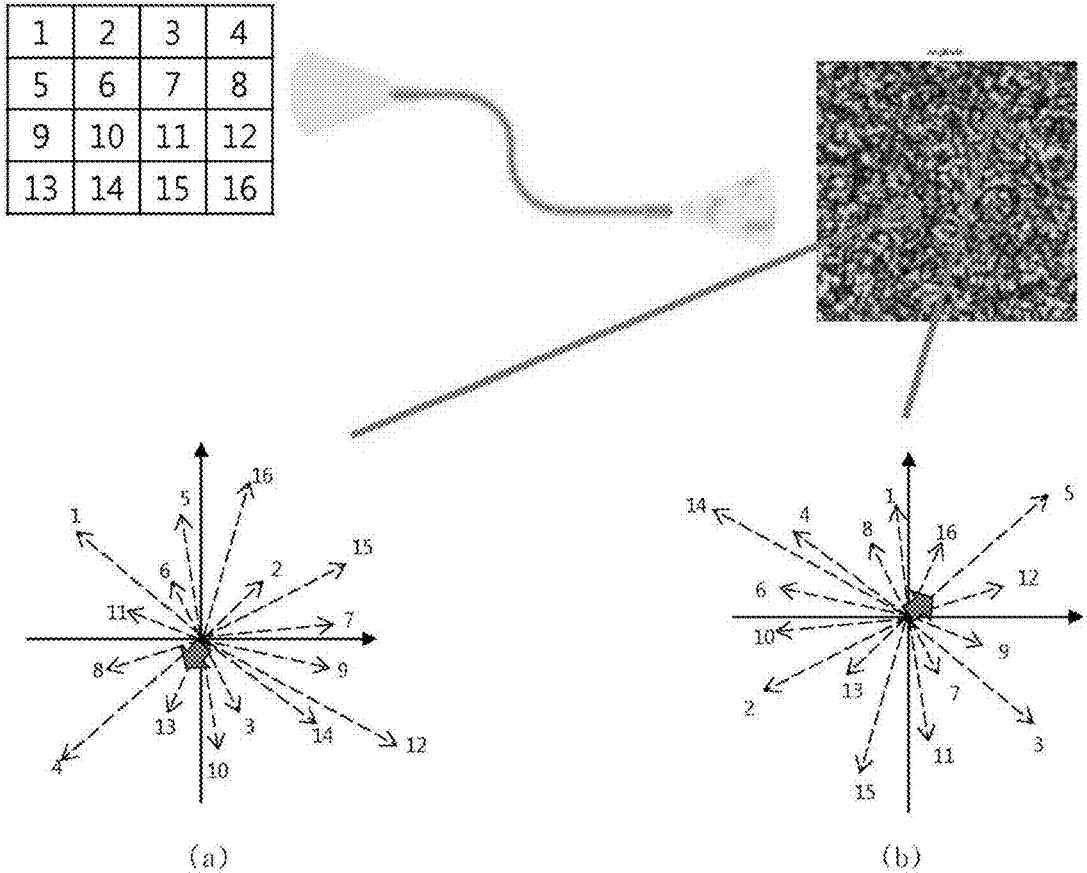

As shown in FIG. 5, if light penetrates the optical transfer medium 140 while all of 16 unit mirrors are on, the penetrated light is imaged as shown in the right part of FIG. 5. Here, the transmission matrix having the transmission characteristics of the optical transfer medium 140 comprises information of phase and size for each unit mirror at specific points of the imaged image.

FIGS. 5 (a) and (b) schematically show information of phase and size for unit mirrors extracted with regard to two specific points. As shown in the figure, if light penetrates the optical transfer medium 140 and then is imaged, all unit mirrors are associated with specific points of the image.

Figure 6:
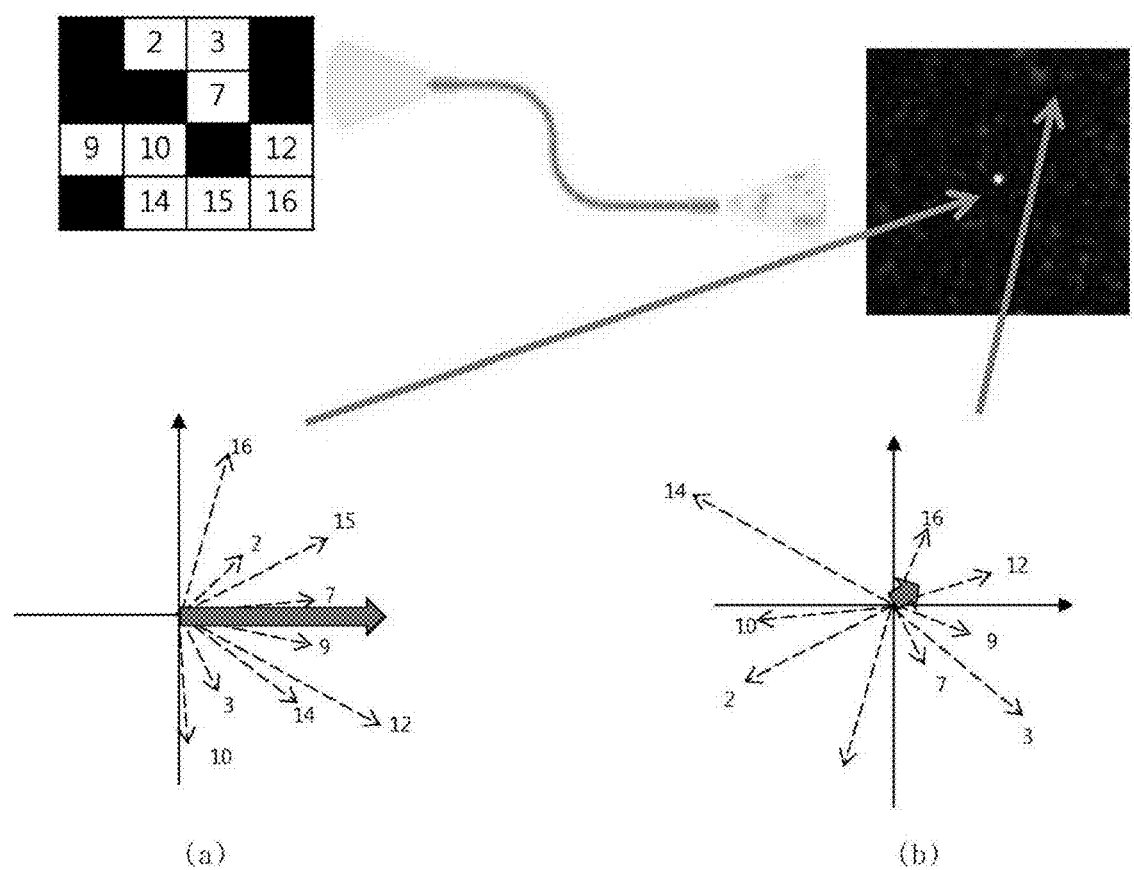

Here, based on FIG. 5(a), if on/off pattern of the unit mirror is decided such that the specific point for FIG. 5 (a) has the brightest light, light can be focused on the corresponding specific point as can be seen in FIG. 6 (a).

For this, focusing pattern light for one specific point is determined such that unit mirrors which reflected light forming constructive interference at the corresponding specific point are turned on. In FIG. 5(a), if unit mirrors having phase from 90° to 270° are turned off (see FIG. 6), the corresponding focusing pattern light penetrates the optical transfer medium 140 and is focused on the corresponding specific point as shown in FIG. 6.

Figure 7:
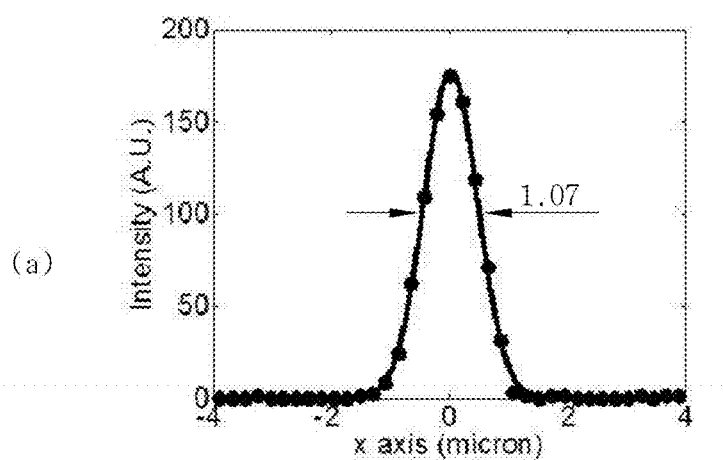
FIG. 7 represents the measurement of light focused by an image acquisition device according to the present invention.
Figure 7:
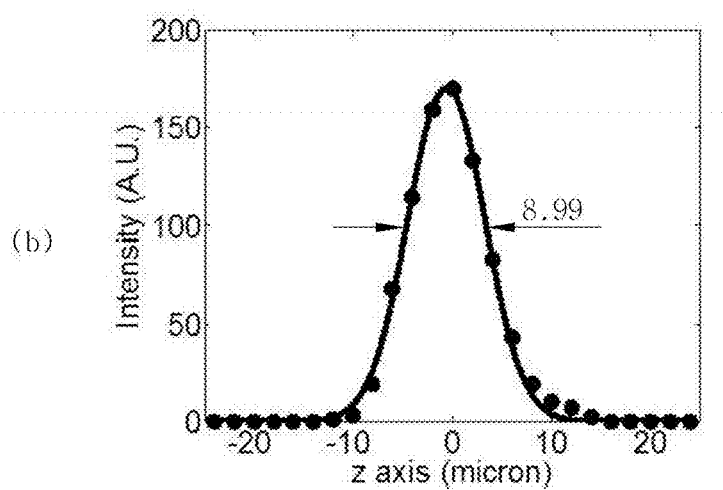

FIG. 7 shows the measurement of light focused on a specific point as described above. As shown in FIG. 7(a), the side resolution is about 1.07 μm, and the axial resolution is about 8.99 μm. The numerical aperture (NA) is about 0.38 and in turn, higher resolution can be obtained than the case in which resolution is determined based on the number of the optical fiber of the bundled fiber.

The measurement of the transmission matrix of the optical transfer medium 140 and the generation of the focusing pattern light as described above can be applied to various type of the optical transfer medium 140. For the optical transfer medium 140, a medium which has light distortion inside the medium and which is applied to the image acquisition can be used. Further to the above optical fiber, a graded index lens having cylinder shape or a thin needle of a micron order used in the ophthalmology can be used in the form of a light guide.

The graded index lens or thin needle cannot guarantee good image quality due to high aberration. However, with the measurement of transmission matrix and the use of focusing pattern light according to the present invention, the image scanning as described above generates image having high resolution and high quality can be obtained.

Here, in case that a plurality of optical paths which are independent each other are formed inside the optical transfer medium 140, i.e., in case that the optical transfer medium 140 is an optical fiber bundle having a plurality of optical fibers which form independent optical paths, a mode-mixing is carried out for light penetrating the optical path such that light penetrating each optical path, i.e., light penetrating each optical fiber of an optical fiber bundle, is associated with all specific points.

Referring to FIG. 2, if a focusing pattern light is generated with respect to an optical transfer medium 140 arranged in the image acquisition device according to the present invention by the above method, information about on/off pattern of the unit mirror for generating the corresponding focusing pattern light is recorded on the image acquisition device.

Then, if light is irradiated from the light source unit 110, the digital micro mirror 120 operates based on the recorded on/off pattern of the unit mirror and a plurality of focusing pattern lights are formed subsequently according to the on/off pattern of the unit mirror and then are transferred to the optical transfer medium 140.

Here, if the optical transfer medium 140 according to the invention has a plurality of light paths which are independent each other inside the medium such as an optical fiber bundle, the object lens 160 between the beam splitter 130 and the optical transfer medium 140 is configured such that a mode-mixing is carried out for light penetrating a plurality of optical paths. For example, a mode-mixing of light can be made by adjusting a space between the object lens 160 and the optical transfer medium 140 such that a focusing of the object lens 160 is blurred.

Focusing pattern light formed by the digital micro mirror 120 travels via the object lens 160, penetrates the optical transfer medium 140, and then is irradiated to the object to be measured (OB). As described above, one focusing pattern light is focused on one specific point when it penetrates the optical transfer medium 140, and lights focused on specific points subsequently by a plurality of focusing patterns make scanning of the object to be measured (OB).

Object lights reflected by the object to be measured (OB) through scanning penetrate the optical transfer medium 140 again and then travel into the imaging unit 150 sequentially so that one image is generated by the entire scanned object light.

Figure 8:
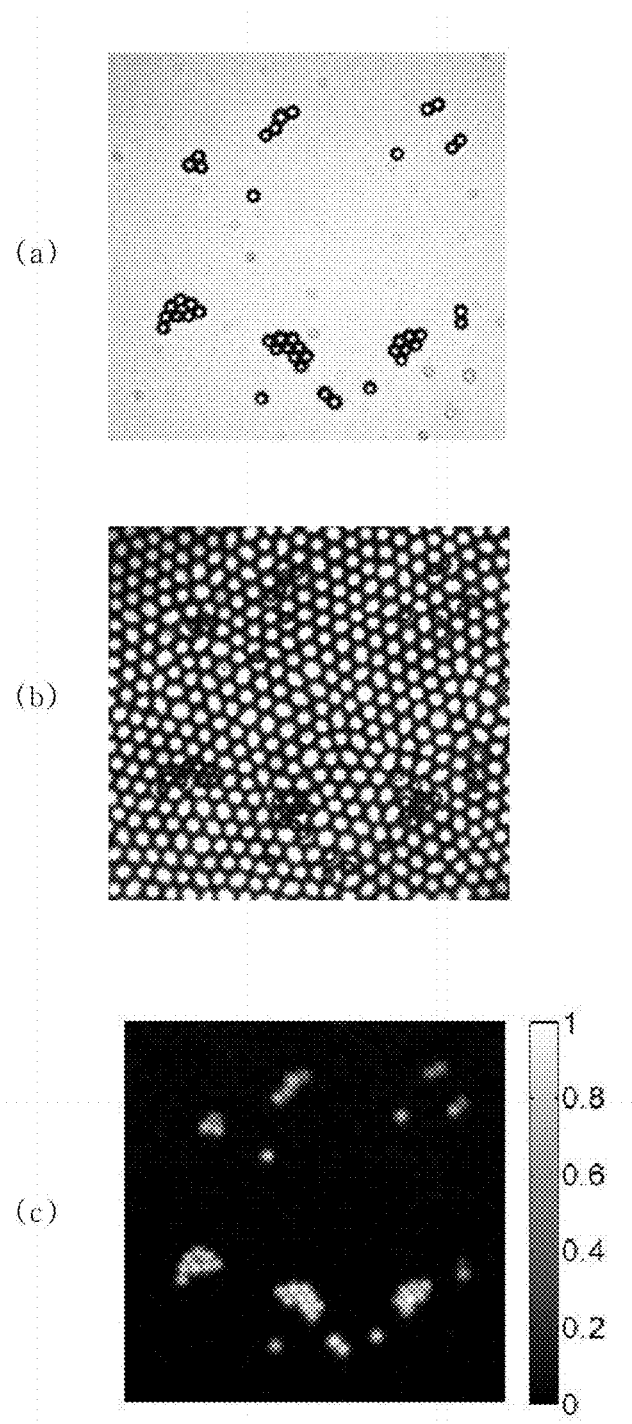
FIGS. 8 and 9 describe the effect of an image acquisition device according to the present invention.
Figure 9:
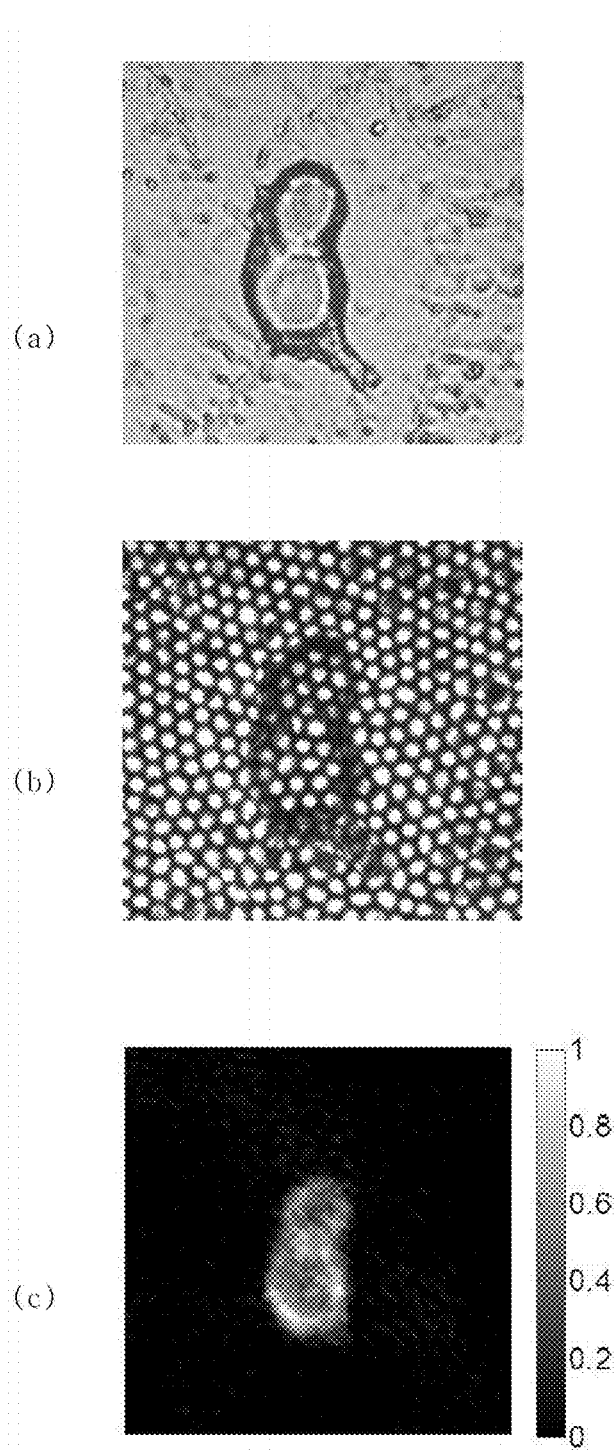

FIGS. 8 and 9 describe the effect of an image acquisition device according to the present invention. FIG. 8(a) shows that the size of a target cell is smaller than the diameter of a prior optical fiber bundle. If the target cell is photographed by an endoscope using the prior optical fiber bundle, an image becomes pixelated and thus, it is difficult to discern a target cell, as can be seen in FIG. 8(b).

Meanwhile, if an image of target cell is taken by the image acquisition device according to the invention, pixelation is avoided and an image having higher resolution can be obtained as can be seen in FIG. 8(c). FIG. 8(c) is an example in which an optical fiber bundle is used as an optical transfer medium 140.

FIG. 9(a) shows a bigger target cell. If the target cell is photographed by an endoscope using the prior optical fiber bundle, it is possible to discern the target cell, but the boundary of cell becomes vague due to pixelation and an image having low resolution is obtained as can be seen in FIG. 9(b).

However, if an image of target cell is taken by the image acquisition device according to the invention, the vagueness of the boundary due to pixelation is completely avoided and an image having higher resolution can be obtained as can be seen in FIG. 9(c).

Meanwhile, in the image acquisition device according to the invention, focusing pattern light can be generated by each distance from the object to be measured (OB).

Figure 10:
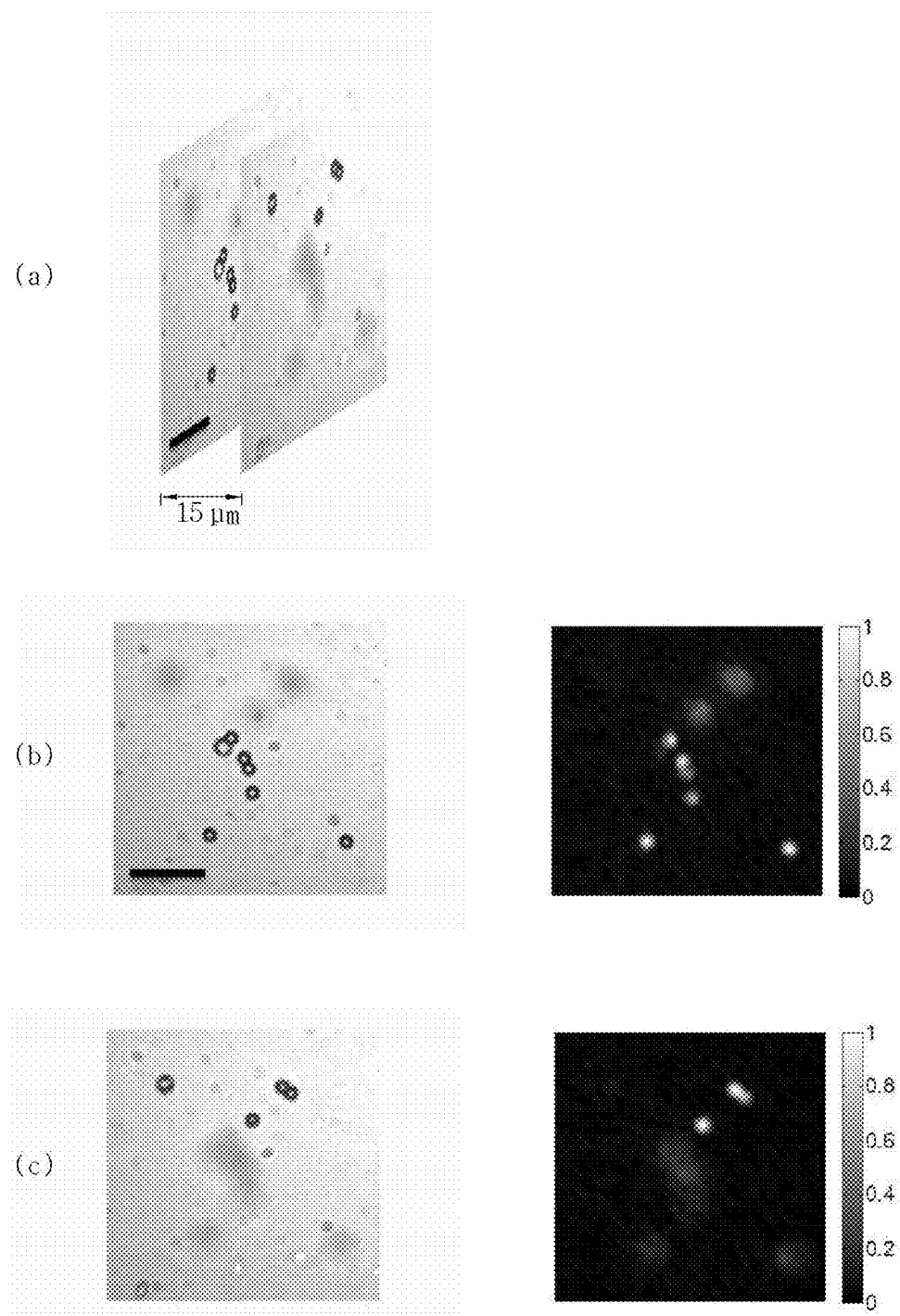
FIG. 10 represents an example of the application of an image acquisition device according to the present invention.

As shown in FIG. 10(a), the depth of a specific point to be focused varies if the object to be measured (OB), i.e., a target cell, is located at another position in a direction that light is irradiated, i.e., in a direction of the depth.

Here, considering the distance to a specific point focused during the generation of focusing pattern light, focusing pattern light for each distance can be generated and recorded. Then, an image is obtained at the first scanning step by focusing pattern lights corresponding to the first distance (see FIG. 10(b)), and then an image is obtained by focusing pattern lights corresponding to the second distance, thereby enabling target cell having different depths to be imaged. By this, the image acquisition device according to the invention can obtain a three-dimensional image. Herein, the focusing pattern light corresponding to the second distance is more easily calculated by using the transmission matrix which is obtained in the process of calculating the focusing pattern light corresponding to the first distance.

In the embodiments described above, as shown in FIG. 2, the image acquisition device according to the invention is an endoscope having an optical fiber bundle. However, the invention is not limited to the above embodiments. Various type of other optical transfer medium can be used for the image acquisition device.

Further, in the embodiments described above, each unit mirror constituting the digital micro mirror 120 is turned on/off independently to generate random pattern light or focusing pattern light. Alternatively, unit mirrors can be turned on/off by N×M unit mirrors which are adjacent each other to generate focusing pattern light.

It is intended that the foregoing descriptions have described only a few of the many possible implementations of the present invention and that variations or modifications of the embodiments apparent to those skilled in the art within the scope and spirit of the invention are embraced within the scope and spirit of the invention.

| List of Reference Numerals | |
|---|---|
| 110: light source unit | 111: light source |
| 120: digital micro mirror | 130: beam splitter |
| 140: optical transfer medium | 150: imaging unit |

INDUSTRIAL APPLICABILITY

A method of measuring transmission characteristics of an optical transfer medium and an image acquisition device using the same according to the invention can be used for medical instruments such as a medical endoscope using optical transfer medium such as an optical fiber or industrial devices for inspecting sewer pipes, an inner part of a collapsed building or an inner structure of a building.

The invention claimed is:

1. A method for measuring transmission characteristics of an optical transfer medium, the method comprising:
    irradiating light from a light source unit;
    reflecting light irradiated from the light source unit by a digital micro mirror and making the light penetrate the optical transfer medium, wherein a plurality of random pattern lights having different wave surfaces are generated subsequently according to an on/off pattern of a plurality of unit mirrors constituting the digital micro mirror;
    imaging transmission light which penetrated the optical transfer medium;
    measuring a transmission matrix for the transmission characteristics of the optical transfer medium based on the plurality of random pattern lights and the imaged transmission light; and
    obtaining a plurality of focusing pattern lights for an on/off pattern of the digital micro mirror based on the transmission matrix,
    wherein a single focusing pattern light is focused on a single specific point when the focusing pattern light penetrates the optical transfer medium, and specific points focused by each of the plurality of focusing pattern lights scan an object to be measured such that the object to be measured is imaged, and
    wherein the transmission matrix comprises phase information of light reflected by each of the plurality of unit mirrors at a specific point of light which penetrated the optical transfer medium, and during the obtaining of the plurality of focusing pattern lights, the focusing pattern light that is for the specific point is obtained such that unit mirrors among the plurality of unit mirrors which reflected light that forms constructive interference at the specific point based on the phase information are turned on.

2. The method according to claim 1, wherein the optical transfer medium comprises, inside the medium, a plurality of light paths which are independent from each other, and during the reflecting of the light, a mode-mixing is made on light which penetrates the plurality of light paths and the light is emitted from the optical transfer medium.

3. The method according to claim 2, wherein the optical transfer medium comprises an optical fiber bundle having a plurality of optical fibers each of which forms each of the plurality of light paths.

4. The method according to claim 1, wherein the optical transfer medium comprises either one or both of a graded index lens having a cylindrical shape, and a medium applied to image acquisition which allows light to penetrate the medium and which generates light distortion inside the medium.

5. The method according to claim 1, wherein the digital micro mirror is configured such that each of the plurality of unit mirrors is turned on/off independently or adjacent unit mirrors among the plurality of unit mirrors are turned on/off by N×M mirrors to form the random pattern light.

6. The method according to claim 1, wherein the obtaining of the plurality of focusing pattern lights comprises obtaining the plurality of focusing pattern lights by each distance from the object to be measured.

7. An image acquisition device, comprising:
a light source configured to irradiate light;
a digital micro mirror including a plurality of unit mirrors, and configured to reflect light irradiated from the light source such that a plurality of predetermined focusing pattern lights having different wave surfaces are generated subsequently according to an on/off pattern of the plurality of unit mirrors;
an optical transfer medium which enables the focusing pattern lights that are formed by the digital micro mirror to penetrate the optical transfer medium, and then move toward an object to be measured;
a sensor configured to image object light which was reflected by the object to be measured and penetrated the optical transfer medium; and
a beam splitter arranged on a light path between the digital micro mirror and the optical transfer medium to direct the focusing pattern light from the digital micro mirror toward the optical transfer medium, and direct the object light which penetrated the optical transfer medium toward the sensor,
wherein a single focusing pattern light is focused on a single specific point when the focusing pattern light penetrates the optical transfer medium, and specific points focused by each of the plurality of focusing pattern lights scan the object to be measured such that the object to be measured is imaged,
wherein each of the plurality of focusing pattern lights is configured to be focused on each of the specific points based on a transmission matrix which is premeasured for the optical transfer medium,
wherein the transmission matrix is measured by
irradiating light from the light source,
reflecting light irradiated from the light source by the digital micro mirror and making the light penetrate the optical transfer medium, wherein a plurality of random pattern lights are generated subsequently according to the on/off pattern of the plurality of unit mirrors,
imaging transmission light which penetrated the optical transfer medium, and
measuring the transmission matrix for the optical transfer medium based on the plurality of random pattern lights and the transmission light imaged, and
wherein the transmission matrix comprises phase information of light reflected by each of the plurality of unit mirrors at a specific point of light which penetrated the optical transfer medium, and the focusing pattern light for the specific point is configured such that unit mirrors among the plurality of unit mirrors that reflected light which forms constructive interference at the specific point based on the phase information are turned on.

8. The image acquisition device according to claim 7, wherein the digital micro mirror is configured such that each of the plurality of unit mirrors is turned on/off independently or adjacent unit mirrors among the plurality of unit mirrors are turned on/off by N×M mirrors to form the random pattern light.

9. The image acquisition device according to claim 7, wherein the optical transfer medium comprises, inside the medium, a plurality of light paths which are independent from each other, and the image acquisition device further comprises an object lens arranged between the beam splitter and the optical transfer medium so that a mode-mixing is made on light which penetrates the plurality of light paths and then the light is emitted from the optical transfer medium.

10. The image acquisition device according to claim 9, wherein the optical transfer medium comprises an optical fiber bundle having a plurality of optical fibers, each of which forms the plurality of light paths.

11. The image acquisition device according to claim 7, wherein the optical transfer medium comprises either one or both of a graded index lens having cylindrical shape and a medium applied to image acquisition which allows light to penetrate the medium and which generates light distortion inside the medium.

12. The image acquisition device according to claim 7, wherein the plurality of focusing pattern lights are obtained and recorded by each distance from the object to be measured.

* * * * *